United States Patent

Sandosham et al.

[11] Patent Number: 6,124,298
[45] Date of Patent: Sep. 26, 2000

[54] PYRAZINEDICARBOXYLIC-ACID DERIVATIVES AS CELL PROLIFERATION REGULATORS

[75] Inventors: Jessie Sandosham, Oslo, Norway; Johann Hiebl; Hermann Kollmann, both of Linz, Austria; Alan Cuthbertson; Peter Fischer, both of Oslo, Norway; Michael Hartmann, Pettenbach, Austria; Peter Kremminger, Asten, Austria; Franz Rovenszky, Linz, Austria; Mette Husbyn, Oslo, Norway

[73] Assignee: Nycomed Imaging AS, Oslo, Norway

[21] Appl. No.: 09/377,776

[22] Filed: Aug. 20, 1999

Related U.S. Application Data

[62] Division of application No. 08/849,456, Jun. 5, 1998, Pat. No. 5,972,926.

[30] Foreign Application Priority Data

Dec. 20, 1994 [GB] United Kingdom .................. 94 25730

[51] Int. Cl.⁷ .................. A61K 31/4965; C07D 241/02; C07D 295/027
[52] U.S. Cl. .................. 514/255.01; 514/183; 544/255
[58] Field of Search .................. 544/336; 514/255.01

[56] References Cited

U.S. PATENT DOCUMENTS 5,972,926  10/1999  Sandosham et al. .................. 514/185

FOREIGN PATENT DOCUMENTS

| 93/13789 | 7/1993 | WIPO . |
| 93/24522 | 12/1993 | WIPO . |
| 93/24524 | 12/1993 | WIPO . |
| 95 01990 | 1/1995 | WIPO . |
| 95/11693 | 5/1995 | WIPO . |
| 95/15336 | 6/1995 | WIPO . |

OTHER PUBLICATIONS

Wang et al., *J. Med. Chem.*, vol. 35, No. 15, 1992, pp. 2890–2896.

*Primary Examiner*—Mukund J. Shah
*Assistant Examiner*—Pavanaram K Sripada
*Attorney, Agent, or Firm*—Bacon & Thomas

[57] ABSTRACT

The present invention relates to novel pyrazine compounds and their use in the regulation of haematopoiesis, in particular in the stimulation of haematopoiesis, and in the treatment of bacterial, viral and fungal diseases.

9 Claims, No Drawings

PYRAZINEDICARBOXYLIC-ACID DERIVATIVES AS CELL PROLIFERATION REGULATORS

This application is a division of application Ser. No. 08/849,456 filed Jun. 5, 1998, U.S. Pat. No. 5,972,926.

The present invention relates to novel pyridine or pyrazine compounds and their use in the regulation of haematopoiesis, in particular in the stimulation of haematopoiesis, and in the treatment of bacterial, viral and fungal diseases.

The mammalian body contains cells having enormously diverse structures and functions, and the mechanisms of differentiation and development have been the focus of much study. It is known that for systems of cells having a continuous turnover the mechanism commonly involves a reservoir of pluripotent stem cells which divide and constantly supply new cells to the system. While initially homogeneous the stem cells supplied from the "reservoir" soon become committed to one or other morphology and subsequently develop into the required functional cells.

One example of such a stem cell system is the haemopoietic system in bone marrow.

The manipulation or control of stem cell division is of great potential therapeutically and much research continues to be devoted to elucidating the mechanisms involved and the chemical messengers responsible. To date several biomolecules have been identified as possessing a role in cell production and differentiation either by the stimulation or inhibition of a step within the process. Myelopoiesis has been particularly well studied in this regard and molecules involved in its control include: colony-stimulating factors (CSF) such as granulocyte colony-stimulating factor (G-CSF), macrophage colony-stimulating factor (M-CSF), granulocyte-macrophage colony-stimulating factor (GM-CSF), multi-lineage colony-stimulating factor (multi-CSF; IL-3) [see Metcalf, Science 229: 16 (1985)], interleukin II (IL-II) [see Paul et al Proc Natl Acad Sci USA 87: 7521 (1990)], Lactoferrin [see Broxmeyer et al Blood Cells 11: 429 (1986)], prostaglandins [see Pelus et al J. Immuno 140: 479 (1988)], acidic (H-subunit) ferritin [see Broxmeyer et al Blood 68: 1257 (1986)], inferferons ($\alpha$, $\beta$ and $\gamma$) [see Pelus et al supra. and Broxmeyer et al J. Immuno 131: 1300 (1983)], tumour necosis factors ($\alpha$ and $\beta$) [see Broxmeyer et al J Immunol 136: 4487 (1986)], transforming growth factor-$\beta$ [see Ottman et al J Immunol 140: 2661 (1988)], and activin and inhibin [see Broxmeyer et al Proc Natl Acad Sci USA 86: 779 (1989)].

It has also been found that the haemoregulatory pentapeptide (pEEDCK) inhibits the proliferation of myelopoietic cells selectively [see Paukovits et al Z. Naturforsch 37: 1297 (1982)] and other peptides corresponding to a narrow general formula have been found to exert a similar inhibitor effect in hemopoiesis [see EP-A-112656 and WO90/02753]. Oxidation of the peptide monomers results in dimeric molecules linked by a cysteine bridge and these dimeric molecules have also been found to stimulate myelopoiesis [see Laerum et al. Exp. Hematol 16: 274 (1988)]. The (pEEDCK)$_2$ dimer and other similar compounds are disclosed in WO-A-88/03535.

There is however a continuing need for compounds capable of regulating cell proliferation, in particular haematopoiesis, to a useful level in vivo. In this regard it should be noted that selective stimulation of individual cell types is of particular clinical importance.

The present invention relates to certain novel pyridine and pyrazine-containing compounds capable of regulating, in particular stimulating, haematopoiesis.

Viewed from one aspect the invention provides compounds of formula I:

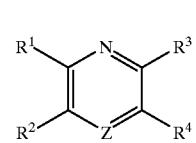

(I)

(wherein
$R^1$ represents a group

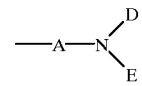

or —G—D;
one of $R^2$, $R^3$ and $R^4$ represents a group as defined above for $R^1$ which may be the same as or different from $R^1$ and the remaining two of $R^2$, $R^3$ and $R^4$ independently represent a hydrogen atom or a $C_{1-6}$ alkyl group;
or $R^1$ and $R^2$ together form a group —CONH—W—NHCO— and $R^3$ and $R^4$ independently represent hydrogen or a $C_{1-6}$ alkyl group;
or $R^3$ and $R^4$ together with the intervening ring carbon atoms norm an aromatic ring and $R^1$ and $R^2$ are both

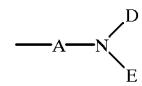

or —G—D;
Z represents —N— or —CH—;
A represents —CO— or —CH$_2$—;
represents cis or trans —CH═CH— or a group of the formula

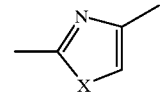

in which X represents —O—, —S—, —NH— or —CH$_2$—;
D represents a group —CR$^5$R$^6$R$^7$ or —CR$^8$[(CH$_2$)$_1$—X']$_2$ in which
$R^5$ represents —H or a $C_{1-4}$ alkyl group optionally substituted by a hydroxy, $C_{1-4}$ alkoxy, carboxy, phenyl or hydroxyphenyl group, such as —CH$_3$, —CH$_2$OH, —CH$_2$OCH$_3$, —CH(CH$_3$)OH, —(CH$_2$)$_2$OH, —CH$_2$(C$_6$H$_4$)OH, —CH$_2$CO$_2$H or —(CH$_2$)$_2$CO$_2$H;
$R^6$ represents —H or —CH$_3$;
$R^7$ represents —CO$_2$R$^9$ or —CONR$^9$R$^9$;
$R^8$ represents —H or a $C_{1-6}$ alkyl group optionally substituted by a hydroxyl group;

X' represents —OH, —NH$_2$, —CO$_2$R$^9$ or —CONR$^9$R$^9$;

each R$^9$ independently represents —H or a C$_{1-6}$ alkyl group;

l is 0 or an integer from 1 to 5;

E represents —H, —OH or C$_{1-6}$ alkyl;

or D and E each represents a group —(CH$_2$)$_k$—X' or —(CH$_2$)$_k$—CO$_2$R$^{10}$ in which k is an integer from 1 to 5, X' has the above meaning and R$^{10}$ represents a C$_{7-10}$ aralkyl group;

or D and E together with the intervening nitrogen atom form a heterocyclic group of formula

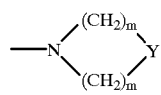

in which each m independently represents an integer from 1 to 3;

Y represents —O—, —NH—, —S—, —SO— or —SO$_2$—;

W represents a straight-chained or branched C$_{1-20}$ alkylene group which may be interrupted by one or more —O— or —NH— groups and which may carry one or more —OH, —NH$_2$ or optionally esterified carboxyl groups or which may carry one or more carbonyl groups adjacent to any interrupting —NH— group, such as a C$_{1-6}$ alkylene group, —CH$_2$—O—(CH$_2$)$_{1-4}$—O—CH$_2$—, —CH(COR$^{11}$)—(CH$_2$)$_{1-6}$—CH(COR$^{11}$)— or —CH(CH$_2$OH)—CO—V—CO—CH(CH$_2$OH)—;

in which each R$^{11}$ independently represents —OH or —NH$_2$; and

V represents —NH—(CH$_2$)$_2$—CONH—(C$_6$H$_4$)—NHCO—(CH$_2$)$_2$—NH—, —NH—CH$_2$—CONH—CH$_2$—(C$_6$H$_4$)—CH$_2$—NHCO—CH$_2$—NH— or —NH—CH(CH$_2$CO$_2$H)—CO—NH—CHR$^{12}$—(CH$_2$)$_4$—CHR$^{12}$—NH—CO—CH(CH$_2$CO$_2$H)—NH— in which R$^{12}$ represents —CO—NH—CH(CO$_2$H)—(CH$_2$)$_4$—NH$_2$)

and physiologically acceptable salts thereof.

Preferred compounds according to the invention ie those of formula I in which R$^1$ and R$^2$ are both

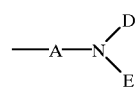

or —G—D;

Particularly preferred compounds of formula I are those in which Z is —N—; R$^1$ and R$^2$ are

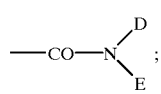

and R$^3$ and R$^4$ are —H.

Especially preferred compounds include:

Pyrazine-2,3-dicarboxyl-di[D-Ser-OH]:

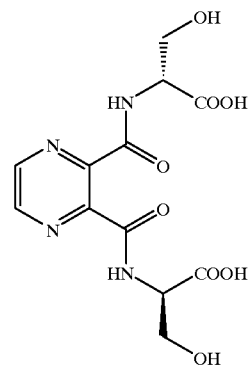

N,N,N',N'-tetrakis(2-hydroxyethyl)pyrazine-2,3-dicarboxamide:

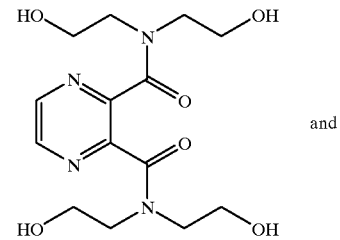

and

N,N'-bis(1,3-dihydroxyprop-2-yl)pyrazine-2,3-dicarboxamide.

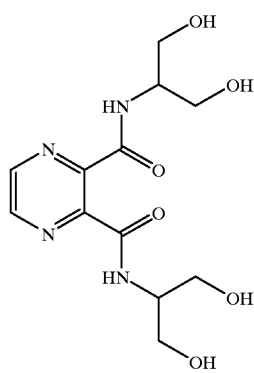

These especially preferred compounds have in common some particularly advantageous properties, such as low molecular mass, semi-peptidic or non-peptidic nature and the presence of minimal or no chirality. It can thus be expected that these compounds will be more easily and inexpensively produced, as well as being less metabolically labile and more amenable to oral administration than other stimulators of the haematopoietic system known in the art, which are generally polypeptides.

One further especially preferred compound of formula I is

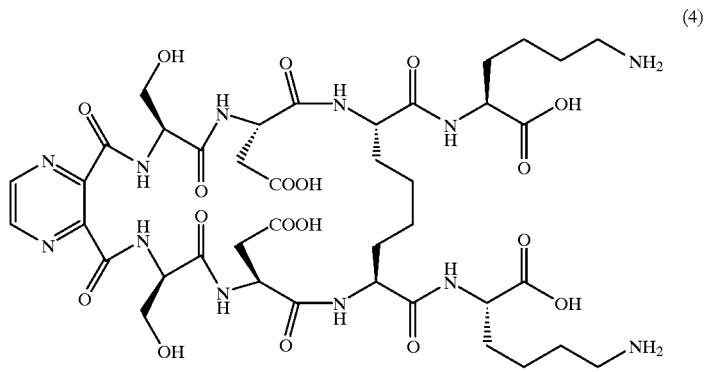

(4)

Pyrazine-2,3-dicarboxyl-[(L-Ser)/(D-Ser)]-(Asp)$_2$-Dasa-(Lys-OH)$_2$.

The compounds of the invention are of use in the regulation, in particular in the stimulation, of haematopoiesis. The compounds may, for example, be used in the stimulation of myelopoiesis in patients suffering from reduced myelopoietic activity, including bone marrow damage, agranulocytosis and aplastic anaemia. This includes treatment of patients having depressed bone marrow function due to immunosuppressive treatment to suppress tissue reactions, e.g. in bone marrow transplant surgery.

The compounds may also be used to promote more rapid regeneration of bone marrow after cytostatic chemotherapy and radiation therapy for neoplastic and viral diseases.

In addition, the new compounds may be of particular value where patients have serious infections due to lack of immune response following bone marrow failure.

Another clinical application will be in combination with known peptide monomers such as those described in EP-A-0359338, WO-A-93/10807 and WO-A-93/24524 to selectively stimulate or inhibit the activity of haematopoietic cells, eg. bone marrow cells. Use of the new compounds in this way induces alternating peaks of high and low activity in the bone marrow cells, thus augmenting the natural circadian rhytm of haemopoiesis. In this way, cytostatic therapy can be given at periods of low bone marrow activity, thus reducing the risk of bone marrow damage, while regeneration will be promoted by the succeeding peak of activity.

A further clinical application of the compounds of the invention is in the treatment of bacterial, fungal and viral diseases caused by haematopoietic disturbances, such as Candida and Herpes.

In general, in order to exert a stimulatory effect, the compounds of the invention may be administered to human patients orally or by injection in the dose range 0.001–100 mg, for example 1–5 mg, per 70 kg body weight per day. If administered intravenously or subcutaneously, the dose may be in the range 1–10 mg per 70 kg body weight per day, for example about 6 mg, for up to ten days. Nasal, topical (transdermal) or rectal administration is, of course, also feasible. In principle it is desirable to produce a concentration of the compound of about $10^{-13}$ M to $10^{-5}$M in the extracellular fluid of the patient.

According to a further feature of the present invention there are provided pharmaceutical compositions comprising as active ingredient one or more compounds of formula (I) as hereinbefore defined or physiologically compatible salts thereof, in association with a pharmaceutical carrier or excipient. The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1–10 mg, for example 1–5 mg of the compound of formula (I) or salt thereof.

The present invention thus provides compounds of formula I and compositions thereof for use in the regulation of haematopoiesis. Use of the compounds according to the invention in the manufacture of a medicament to regulate haematopoiesis forms a further aspect of the invention. Inhibition and stimulation of bone marrow regeneration are of particular interest.

According to a still further feature of the present invention there is provided a method of regulation of haematopoiesis, especially myelopoiesis which comprises administering an effective amount of a pharmaceutical composition as hereinbefore defined to a subject.

The present invention also provides a process for the preparation of compounds of formula I, said process comprising any one of the following steps:

(a) (in order to prepare compounds of formula I in which $R^1$ and one of $R^2$, $R^3$ and $R^4$ represents

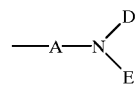

in which A is —CO—) reacting the corresponding pyridine or pyrazine 2,3-, 2,5- or 2,6-dicarboxylic acids, esters or an activated derivative thereof with a group of formula II (II)

(wherein D and E are as hereinbefore defined);

(b) (in order to prepare compounds of formula I in which $R^1$ and one of $R^2$, $R^3$ and $R^4$ represents

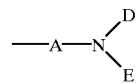

in which A is —CH$_2$—) reacting the corresponding pyridine or pyrazine 2,3-, 2,5- or 2,6-bis(chloromethyl) derivative with a group of formula II as hereinbefore defined;

(c) (in order to prepare compounds of formula I in which $R^1$ and one of $R^2$, $R^3$ and $R^4$ represents —G—D in which G is cis or trans —CH═CH—) reacting the corresponding pyridine or pyrazine 2,3-, 2,5- or 2,6-dialdehyde with a phosphorus ylid of formula III (III)

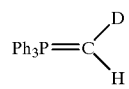

Such a pyridine or pyrazine dialdehyde may conveniently be obtained from the corresponding dicarboxylic acids, diacid derivatives, dialcohols, diacetals etc.

(d) (in order to prepare compounds of formula I in which $R^1$ and one of $R^2$, $R^3$ and $R^4$ represents —G—D in which G is a group of formula

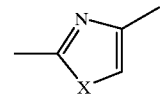

reacting the corresponding pyridine or pyrazine 2,3-, 2,5- or 2,6-dicarboxylic acids or an activated derivative thereof such as imino esters, nitriles etc. with a group of formula IV (IV)

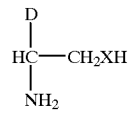

(wherein X and D are as hereinbefore defined) followed where necessary by oxidation;

(e) (in order to prepare compounds of formula I in which $R^1$ and $R^2$ together form a group —CO—NH—W—NH—CO— where W is as hereinbefore defined) reacting a diamine of formula H$_2$N—W—NH$_2$ with a pyridine or pyrazine 2,3-dicarboxylic acid or an activated derivative thereof or 2,3-carboxylic anhydride;

(f) (in order to prepare compounds of formula I in which $R^3$ and $R^4$ together with the carbon atoms to which they are attached represent an aromatic ring) a bicyclic aromatic compound such as quinoline 2,3-dicarboxylic acid or its anhydride may be used in methods (a) or (d);

(g) converting a compound of formula I as prepared in any one of steps (a) to (c) into a salt thereof; and (h) resolving a chiral compound of formula I into its isomers.

In the reactions described above any reactive groups present, such as hydroxy, carboxy, amino etc. may optionally be protected during the reaction by means of conventional protecting groups which are cleaved again after the reaction.

Optionally, the final step in the synthesis of compounds of formula I will thus be deprotection of a fully or partly protected derivative of a compound of formula I and such processes form a further aspect of the invention.

Suitable hydroxy protecting groups include trimethylsilyl, acetyl, benzoyl, tert.butyl, trityl and benzyl.

Carboxyl protecting groups which may be used include, for example trimethylsilyl, methyl, ethyl, tert.butyl and benzyl.

Amino protecting groups which may be employed include 9-fluorenylmethoxycarbonyl (Fmoc-), t-butoxycarbonyl (Boc-) and carbobenzoxy.

The subsequent cleaving of any protecting group used may be carried out by appropriate methods known in the art. For example, a tert.butyl or tert.butyloxycarbonyl group is preferably cleaved by treating with an acid such as trifluoroacetic acid or hydrochloric acid, optionally using a solvent such as methylene chloride.

The reaction of step (a) is conveniently carried out in a solvent or mixture of solvents such as ethanol, methylene chloride or dimethylformamide.

The carbonyl groups will generally be converted to an activated form for example by reaction with an activating reagent such as PyBOP (benzotriazole-1-yl-oxy-tris-pyrrolidino-phosphonium hexafluorophosphate) or a diimide reagent such as DCC (dicyclohexylcarbodiimide) or DIC (diisopropylcarbodiimide), in the presence of a base such as N-methylmorpholine. A di-ester, e.g. di-$C_{1-6}$ alkylester may also be used.

In the case of preparation of the 2,3-disubstituted pyridine or pyrazine compounds the corresponding anhydrides may be used in step (a) in place of the 2,3-dicarboxylic acids or esters as starting material. The amine reacted with the dicarboxylic acid derivative may conveniently be supported on a solid phase during the acylation reaction.

In the reaction of step (c), the compound of formula III may be prepared by treatment of a phosphonium salt, such as triphenylphosphonium chloride, with a base, such as BuLi, the phosphonium salt conveniently being synthesised from the phosphine and an alkyl halide.

As mentioned above the compounds of formula I may be resolved into their geometric or optical isomers. Thus, for example, cis/trans mixtures may be resolved into their cis and trans isomers, and those compounds having at least one optically active carbon atom may be resolved into their enantiomers.

Thus, for example, the cis/trans mixtures obtained may be resolved by chromatography into the cis and trans isomers and the compounds of formula I which occur in racemate form may be separated by known methods, e.g. chromatography, into the diastereoisomers thereof which, if they occur in racemic form, may subsequently be separated into the enantiomers, eg. by chiral chromatography.

The biological activity of the compounds of formula I are demonstrated by the following test:

The murine bone marrow-derived stromal cell line C6.4, which does not constitutively produce any detectable HSF activity, was cultured to confluency during 4 days. The cells were then washed and the media replaced with fresh serum-free media. Compounds 1–6 below (1 μg/mL) were then added and after 24 h incubation the culture supernatants were passed through 30 kDa cut-off filtration devices in order to remove known high molecular mass colony stimulating factors (CSF). Murine bone marrow cells were cultured ($7.5 \times 10^4$ cells in medium containing 15% fetal calf serum and 0.3% agar) in the presence of sub-optimal concentrations of Granulocyte-Macrophage (GM)-CSF (20 U/mL). Serial dilutions of the filtered C6.4 cell supernatants were then added and the agar plates were incubated at 37° C. under 5% $CO_2$ for 7–8 days. Colonies of proliferating bone marrow cells were counted using a microscope. HSF units were calculated as follows: [(Colony number in sample)-(Colony number in -ve control)/C.64 cell supernatant filtrate dilution factor].

| Compound | HSF* units/mL |
|---|---|
| 1 Pyrazine-2,3-dicarboxyl-di[D-Ser-OH] | $1.9 \times 10^6$ |
| 2 N,N,N',N'-tetrakis(2-hydroxyethyl)pyrazine-2,3-dicarboxamide | $2.2 \times 10^6$ |
| 3 N,N'-bis(1,3-dihydroxyprop-2-yl)pyrazine-2,3-dicarboxamide | $8.7 \times 10^6$ |
| 4 Pyrazine-2,3-dicarboxyl-[(L-Ser)/(D-Ser)]-(Asp)$_2$-Dasa-(Lys-OH)$_2$ | $5.2 \times 10^5$ |
| Positive Control a | $1.5 \times 10^6$ |
| Negative Control b | 0 |

*Haematopoietic Stimulating Factor a) The peptide (Glp-Glu-Asp)$_2$-L,L-2,6-diaminosuberyl (Lys-OH)$_2$ was used:

The capacity of this peptide to enhance myelopoiesis through stimulation of stromal cell cytokine production has been demonstrated both in vitro and in vivo: L. M. Pelus et al., Exp. Hematol., 1994, 22:239–247.

b) No compound addition to C6.4 cells but a corresponding volume of diluent (phosphate-buffered saline).

The following Examples are given by way of illustration only.

Throughout the following Examples, abbreviations for amino acids are according to conventions (see Eur. J. Biochem. 1984, 138: 9–37). Amino acids are of the L-series unless otherwise indicated.

The following abbreviations are used in the Examples:

| | |
|---|---|
| Dasa = | L,L-2,7-Diaminosuberic acid |
| DCC = | Dicyclohexylcarbodiimide |
| DIC = | Diisopropylcarbodiimide |
| DMF = | N,N-Dimethylformamide |
| DMSO = | Dimethylsulphoxide |
| FAB-MS = | Fast atom bombardment mass spectrometry |
| Fmoc = | 9-Fluorenylmethoxycarbonyl |
| HOBt = | 1-Hydroxybenzotriazole |
| NMM = | N-Methylmorpholine |
| NMR = | Nuclear magnetic resonance spectroscopy |
| PyBop = | Benzotriazole-1-yl-oxy-tris-pyrrolidino-phosphonium hexa-fluorophosphate |

EXAMPLE 1

Pyrazine-2,3-dicarboxyl-[D-Ser-OH]/(L-Ser-OH)

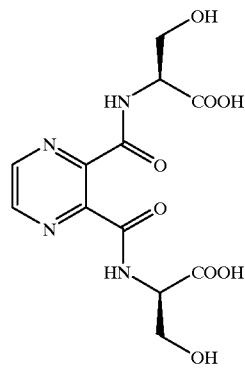

Pyrazine-2,3-dicarboxylic acid (0.26 g, 1.6 mmol), PyBOP (1.6 g, 3.2 mmol), HOBt (0.43 g, 3.2 mmol) and NMM (0.53 mL, 4.7 mmol), dissolved in $CH_2Cl_2$(10 mL), were allowed to react for 5 min. A solution of H-Ser(Bu$^t$)-OMe, HCl (1 g, 4.7 mmol) and NMM (0.53 mL, 4.7 mmol) in $CH_2Cl_2$ (20 mL) was then added and the entire mixture was stirred overnight. The solution was then extracted successively with 5% aq $NaHCO_3$ and brine, dried over anhydrous $MgSO_4$, filtered and evaporated to yield an oily residue of pyrazine-2,3-dicarboxyl-di-[Ser(Bu$^t$)-OMe], TLC $R_f$=0.72 (90:10:0.5:1 $CHCl_3$/MeOH/AcOH/$H_2O$).

This material (ca. 1.6 mmol) was dissolved in MeOH (20 mL) and 2M aq NaOH (3.2 mL, 6.4 mmol) was added. The reaction mixture was stirred until TLC indicated complete methyl ester hydrolysis after 1.5 h ($R_f$=0.28 only). The solution was concentrated to remove MeOH. It was then diluted with $H_2O$ and acidified to pH 2 with 6 M aq HCl. The precipitate was extracted into $CHCl_3$ and the combined extracts were dried over anhydrous $MgSO_4$, filtered and evaporated to dryness. Pyrazine-2,3-dicarboxyl-di-[Ser(Bu$^t$)-OH] (0.8 g, 87% was obtained as an oil. Analytical RP-HPLC and FAB-MS analysis indicated that a mixture of two diastereomers was present. One of these ($t_R$=18.5 min; Vydac 218TP54, 4.6×25 mm, 1 mL/min, 5 to 50% MeCN in 0.1% Aq $CF_3COOH$ over 20 min) was optically active (after isolation by RP-HPLC and t-butyl ether deprotection) and consisted of a mixture of the D/D-Ser and L/L-Ser enantiomers of pyrazine-2,3-dicarboxyl-di-[Ser (Bu$^t$)-OH] (chromatographically identical to authentic materials, see below). The other ($t_R$=19.8 min) was meso-pyrazine-2,3-dicarboxyl-di-[Ser(Bu$^t$)-OH], which was purified to homogeneity by preparative RP-HPLC. After lyophilisation the residue was treated for 30 min with a 1:1 mixture of $CF_3COOH$ and $CH_2Cl_2$. This solution was evaporated to dryness and the residue was lyophilised from water solution to yield pure meso-pyrazine-2,3-dicarboxyl-di-[Ser-OH] after preparative RP-HPLC (gradient elution 0 to 6% MeCN in 0.1% aq $CF_3COOH$ on $C_{18}$ column, (NMR spectra consistent with structure), $[\alpha]_D$=0 (c 1, DMF). FAB-MS $[M+H]^+$=343, $C_{12}H_{14}N_4O_8$=342.26.

EXAMPLE 2

Pyrazine-2,3-dicarboxyl-di-[D-Ser-OH]

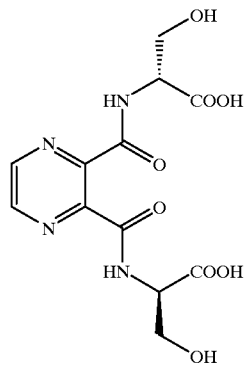

Pyrazine-2,3-dicarboxylic acid (1 g, 6 mmol) was activated with DIC (0.93 mL, 6 mmol) in DMF (15 mL) for 10 min to form the anhydride in situ. To this was added a solution of H-D-Ser(Bu$^t$)-OBu$^t$.HCl (1.7 g, 6.6 mmol) and NMM (0.69 mL, 6.6 mmol) in DMF (10 mL). The mixture was stirred for 4 h. A second portion of H-D-Ser(Bu$^t$)-OBu$^t$.HCl and NMM in DMF (same quantities as above) was then preactivated for 10 min by addition of HOBt (0.81 g, 6 mmol) and DIC (0.93 mL, 6 mmol). This solution was then added to the above mixture and stirred overnight. Solvent was removed in vacuo and the residue was redissolved in $CH_2Cl_2$, extracted with 5% aq $NaHCO_3$, dried over anhydrous $MgSO_4$, filtered and evaporated. The resulting oil was chromatographed on silica gel (70:25:5 hexane/EtOAc/AcOH) and the fractions containing pure pyrazine-2,3-dicarboxyl-di-[D-Ser(Bu$^t$)-OBu$^t$] were pooled and evaporated. The residue was treated for 30 min with $CF_3COOH$ containing 5% $H_2O$; evaporated, redissolved in $H_2O$ and lyophilised. Pure pyrazine-2,3-dicarboxyl-di-[D-Ser-OH] (350 mg, 17%) was obtained after preparative RP-HPLC. $[\alpha]_D$=−17 (c 1, DMF).

$^1$H-NMR (300 MHz, DMSO): δ=3.75–3.8 (m, 4H, C$\underline{H}_2$), 4.46–4.49 (m, 2H, C$^\alpha \underline{H}$), 8.65 (d, J=9 Hz, 2H, 2H, CON$\underline{H}$), 8.82 (s, 2H, aromatic C$\underline{H}$), 12.8 (broad s, 2H, COO$\underline{H}$); $^{13}$C-NMR (75 MHz, DMSO): δ=55.05 ($\underline{C}^\alpha$H), 61.71 ($\underline{C}H_2$), 145.14, 146.0 (aromatic $\underline{C}$H), 164.26 ($\underline{C}$ONH), 171.86 ($\underline{C}$OOH); FAB-MS $[M+H]^+$=343, $C_{12}H_{14}N_4O_8$=342.26.

EXAMPLE 3

Pyrazine-2,3-dicarhoxyl-di-[L-Ser-OH]

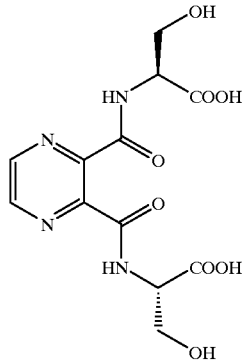

This compound was prepared analogously to the Pyrazine-2,3-dicarboxylate-di-[D-Ser-OH] isomer of Example 2 from H-L-Ser(Bu$^t$)-OBu$^t$.HCl. It had identical analytical data to the isomer of Example 2 with the exception of optical rotation: $[\alpha]_D$=+17 (c 1, DMF).

EXAMPLE 4

Pyrazine-2,3-dicarboxyl-di-[D-Ser-NH$_2$]

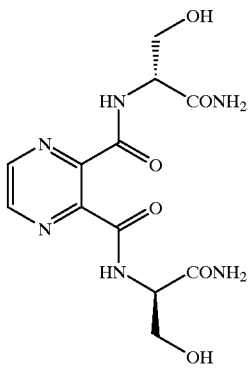

Fmoc-protected Rink amide AM resin (1 g, 0.49 mmol; Novabiochem AG Läufelfingen, Switzerland; see H. Rink, Tetrahedron Lett. 28; 3787–3790 (1987)) was washed with DMF and deprotected with 20% piperidine/DMF. After repeated washing with DMF, Fmoc-D-Ser(Bu$^t$)-OH (776 mg, 2 mmol), PyBOP (1.05 g, 2 mmol), HOBt (306 mg, 2 mmol) and Pr$^i_2$NEt (0.61 mL, 3 mmol) in DMF (5 mL) were added to the resin and allowed to react overnight with agitation of the reaction vessel. The resin was again Fmoc-deprotected and washed before pyrazine-2,3-dicarboxylic acid (27 mg, 0.16 mmol) with the same quantities of PyBOP, HOBt and Pr$^i_2$NEt was coupled overnight in a similar fashion. The resin was then washed successively with DMF and CH$_2$Cl$_2$ and treated 2 h with CF$_3$COOH/H$_2$O/1,2-ethanediol (90:5:5 v/v/v). Resin residue was filtered off and the filtrate was evaporated. The crude peptide material was obtained by precipitation with Et$_2$O. This was dried, redissolved in H$_2$O and chromatographed (Vydac 218TP1022, 22×250 mm, 5 mL/min, isocratic elution 0.1% aq CF$_3$COOH). Appropriate fractions were collected, pooled and lyophilised to yield the pure title compound. Analytical RP-HPLC: $t_R$=3.7 min (Vydac 218TP54, 4.6×250 mm, 1 mL/min, 0 to 20% MeCN in 0.1% aq CF$_3$COOH over 20 min, λ=215 nm). FAB-MS: [M+H]$^+$=341.1, C$_{12}$H$_{16}$N$_6$O$_6$=340.30.

EXAMPLE 5

Pyridine-2,3-dicarboxyl-di-[D-Ser-OH]

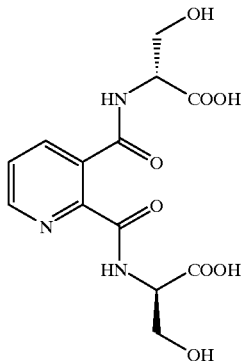

This compound was prepared analogously to the Pyrazine-2,3-dicarboxyl-di-[D-Ser-OH] compound of Example 2 from quinolinic anhydride. The intermediate quinolinoyl-di-[D-Ser(Bu$^t$)-OBu$^t$] had NMR spectra consistent with the proposed structure and RP-HPLC $t_R$=16.1 min (Vydac 218TP54, 4.6×250 mm, 1 mL/min, 50–80% MeCN in 0.1% aq CF$_3$COOH over 20 min). The final product quinolinoyl-di-[D-Ser-OH] was >90% pure (RP-HPLC $t_R$=6.1 min, 0–12% MeCN over 20 min, λ=215 nm). MALDI-TOF MS: [M+H]$^+$=342.3, [M+Na]$^+$=364.3, C$_{13}$H$_{15}$N$_3$O$_8$=341.28.

EXAMPLE 6

Pyrazine-2,5-dicarboxyl-di-[D-Ser-OH]

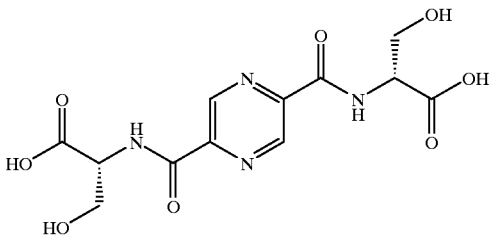

This compound was synthesised from pyrazine-2,5-dicarboxylic acid and H-D Ser(Bu$^t$)-OBu$^t$in a manner analogous to the pyrazine-2,3-dicarboxyl-di-[D-Ser-OH] compound of Example 2. The intermediate pyrazine-2,5-dicarboxyl-di-[D-Ser(Bu$^t$)-OBu$^t$] showed $^1$H-NMR (CDCl$_3$, 300 MHz): δ=1.11 (s, 18 H, CH$_2$OC(CH$_3$)$_3$), 1.42 (s, 18H, C(O)OC(CH$_3$)$_3$), 3.63–3.83 (dm, 4 H, CβH$_2$), 4.60 (m, 2H, C$^\alpha$H), 8.54 (d, 2H, CONH), 9.27 (s, 2H, Ar—H). After removal of the t-butyl protecting groups through CF$_3$COOH treatment, the pure title compound was obtained.

Analytical RP-HPLC: $t_R$=12.5 min (Vydac 218TP54, 4.6× 250 mm, 1 mL/min, 0 to 20% MeCN in 0.1% aq CF$_3$COOH over 20 min, λ=215 nm).

EXAMPLE 7

N,N'-bis-(1,3-dihydroxy-2-methylprop-2-yl) pyrazine-2,3-dicarboxamide

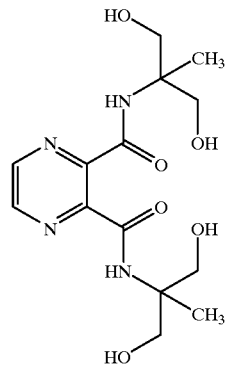

Pyrazine-2,3-dicarboxylic acid (34 mg, 0.2 mmol), PyBOP (229 mg, 0.44 mmol), HOBt (60 mg, 0.44 mmol) and NMM (0.7 mL, 0.64 mmol) were dissolved in DMF (2 mL) and allowed to react for 10 min. 2-Amino-2-methyl-1, 3-propanediol (46 mg, 0.44 mmol) was then added and stirring was continued overnight. The entire reaction mixture was then fractionated on a RP-HPLC column (Vydac 218TP1022, 22×250 mm, 10 mL/min, 0 to 15% MeCN in 0.1% aq $CF_3COOH$ over 40 min). Appropriate fractions were pooled, rechromatographed and lyophilised to yield the pure title compound. Alternatively, the title compound was synthesised as follows: dimethylpyrazine-2,3-dicarboxylate (1.5 g, 7.7 mmol) and 2-amino-2-methyl-1,3-propanediol (1.6 g, 15.4 mmol) in absolute ethanol (5 mL) were heated under reflux during 4 hours. The reaction mixture was then cooled and the solvent was removed under reduced pressure. The residue was chromatographed on a flash silica gel column using $CHCl_3$/MeOH (4:1) as the eluant. Solvents were removed in vacua and the pure title compound (2.2 g, 85%) was obtained after recrystallisation from isopropanol/hexane.

$^1$H-NMR (300 MHz, $CDCl_3$): δ 1.06 (s, 6H, 2×Me), 3.48 (d, J=6.3 Hz, 8H, 4×$CH_2$), 4.29 (t, J=6.3 Hz, 4H, 4×—OH), 7.64 (s, 2H, 2×NH), 8.38 (s, 2H, 2×CH). $^{13}$C-NMR (75 MHz, $CDCl_3$): δ 164.26 (CO), 145.54 (C-2,3), 143.59 (C-5,6), 65.30 ($CH_2$), 58.66 (Cq), 18.13 (Me).

Analytical RP-HPLC: $t_R$=12.28 min (Vydac 218TP54, 4.6×250 mm, 1 mL/min, 0 to 10% MeCN in 0.1% aq $CF_3COOH$ over 20 min, λ=215 nm).

FAB-MS: $[M+H]^+$=343, $C_{14}H_{22}N_4O_6$=342.35.

EXAMPLE 8 pyrazine-2,3-dicarboxyl-[Gly-OH)/(D-Ser-OH)]

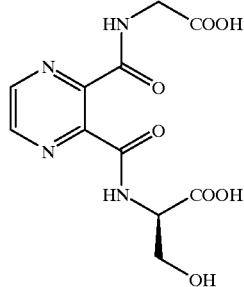

Fmoc-Gly-[TentaGel S Trityl Resin] (1 g, 0.26 mmol; Rapp Polymere GmbH, Tübingen, Germany) was washed with DMF and treated with 20% piperidine/DMF (2×10 mL, 3 min each) to remove Fmoc protecting groups. The resin was again washed with DMF, drained and then reacted with a pre-activated (10 min) mixture of pyrazine-2,3-dicarboxylic acid (336 mg, 2 mmol) and DIC (155 μL, 1 mmol) in DMF (5 mL) for 2 h (-ve Kaiser ninhydrin test at this point). PyBOP (520 mg, 1 mmol), HOBt (135 mg, 1 mmol) and NMM (155 μL, 1.5 mmol) in DMF (5 mL) were then added to the resin, followed after a few min by H-D-Ser(Bu$^t$)-OBu$^t$ (254 mg, 1 mmol) and NMM (110 μL, 1 mmol) in DMF (5 mL). The peptidyl resin mixture was agitated with a stream of $N_2$ overnight. The resin was then washed with DMF and $CH_2Cl_2$ and was drained.

Pyrazine-2,3-dicarboxyl-[(Gly-OH)/(D-Ser(Bu$^t$)-OBu$^t$)] was detached from the synthesis resin by agitation with a solution (50 mL) of 10:10:1 AcOH/$CH_2Cl_2$/MeOH for 2 h. The solution was then filtered off and the resin washed with more neat $CH_2Cl_2$. The combined filtrate and washings were rotary evaporated and the product precipitated by the addition of $Et_2O$ and cooling. The precipitate was collected and dried. An aliquot was redissolved in $H_2O$/MeCN and was chromatographed on a RP-HPLC column (Vydac 218TP1022, 22×250 mm, 10 mL/min, 5–50% MeCN in 0.1% aq $CF_3COOH$ over 50 min). Appropriate fractions were collected, pooled and lyophilised. The product of pyrazine-2,3-dicarboxyl-[(Gly-OH)/D-Ser(Bu$^t$)-OBu$^t$)] had NMR spectra consistent with the proposed structure and was >99% pure ($t_R$=21.6 min on Vydac 218TP54, 4.6×250 mm, 1 mL/min, 5–50% MeCN in 0.1% aq $CF_3COOH$ over 20 min, λ=215 nm).

This material was deprotected by treatment for 1 h with excess $CF_3COOH$ containing 2% $H_2O$. The solution was evaporated and pyrazine-2,3-dicarboxyl-[(Gly-OH)/(D-Ser-OH)] was precipitated by addition of $Et_2O$. The product was dried and lyophilised from $H_2O$. Analytical RP-HPLC: $t_R$=4.7 min, >99% purity (Vydac 218TP54, 4.6×250 mm, 1 mL/min, 0–12% MeCN in 0.1% aq $CF_3COOH$ over 20 min, λ=215 nm). FAB-MS: $[M+H]^+$=313.2, $C_{11}H_{12}N_4O_7$=312.24.

EXAMPLE 9

N,N'-(But-1,4-yl)pyrazine-2,3-dicarboxamide

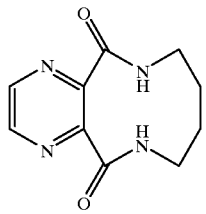

Pyrazine-2,3-dicarboxylic acid (1 g, 6 mmol) was treated with DIC (0.93 mL, 6 mmol) in DMF (20 mL) to form the anhydride in situ. After 10 min the solution was diluted to 50 mL with DMF and 1,4-diaminobutane (0.53 g, 6 mmol) in DMF (10 mL) was added dropwise over 5 min. Soon a solid was observed to precipitate. A solution of PyBOP (3.38 g, 6.5 mmol), HOBt (6.5 mmol) and NMM (1 mL, 9.8 mmol) in DMF (10 mL) was prepared and added slowly to the above suspension (further diluted to 90 mL with DMF). The entire mixture was stirred for 2 h, when dissolution was complete. DMF was then removed under oil-pump vacuum and the resulting paste was redissolved in $CHCl_3$/MeOH (3:1, v/v) and filtered through a silica gel chromatography column. Appropriate fractions were pooled and evaporated. Some residual HOBt was removed as follows: the dried crude product was redissolved in 0.1% aq $CF_3COOH$ and was extracted several times with $Et_2O$. The aqueous phase was then lyophilised and the product chromatographed by RP-HPLC (Vydac 218TP1022, 22×250 mm, 10 mL/min, 0 to 10% MeCN in 0.1% aq $CF_3COOH$ over 40 min) to yield the pure title compound, whose NMR spectra were consistent with the proposed structure. Analytical RP-HPLC: $t_R$=12.06 min (Vydac 218TP54, 4.6×25 mm, 1 mL/min, 0 to 20% MeCN in 0.1% aq $CF_3COOH$ over 20 min, λ=215 nm).

EXAMPLE 10

Pyrazine-2,3-dicarboxyl-[(L-Ser)/(D-Ser)]-(Asp)$_2$-Dasa-(Lys-OH)$_2$ (a) [Fmoc-Asp(OBu$^t$)]$_2$-Dasa-[Lys(Boc)]$_2$-SASRIN resin Fmoc-Lys(Boc)-SASRIN resin (5 g, 0.6 mmol/g) was washed with DMF and then treated with 20% piperidine in DMF for 15 min to remove Fmoc groups. After repeated DMF washing, Fmoc$_2$-Dasa-(OH)$_2$ (648 mg, 1 mmol) was coupled to the deprotected resin with the aid of DCC (1.03 g, 5 mmol) and HOBt (765 mg, 5 mmol) in DMF during 10 h. After washing, a further coupling cycle (1 h) was performed with similar quantities of DCC and HOBt in order to couple any remaining free Dasa carboxyl groups to resin-bound Lys. The dipeptidyl resin was then washed with 30% MeOH/$CH_2Cl_2$ (2×20 min) and DMF. Untreated Lys amino groups were capped by reaction with 10% $Ac_2O$/DMF (2×50 mL) during 1 h. After renewed Fmoc deprotection, acylation with Fmoc-Asp(OBu$^t$)-OPfp (5.78 g, 10 mmol) and HOBt (1.53 g, 10 mmol) was carried out for 2 h. The final product was washed with DMF, $CH_2Cl_2$ and $Et_2O$ before being dried in vacuo. The peptidyl resin contained 0.36 mmol/g amino groups according to spectrophotometric measurement of Fmoc release from an aliquot of resin (Dibenzofulvene-piperidine adduct, $\epsilon_{267}$=18.98, $\epsilon_{301}$=8.550, R. Frank, R. Döring, Tetrahedron, 1988, 44: 6031–6040).

(b) Pyrazine-2,3-dicarboxyl-[(L-Ser)/(D-Ser)]-Asp$_2$-Dasa-(Lys-OH)$_2$

An aliquot of the [Fmoc-Asp(OBu$^t$)]$_2$-Dasa-[Lys(Boc)]$_2$-SASRIN resin (167 mg, 0.06 mmol) was Fmoc deprotected with 20% piperidine/DMF and was washed with DMF. Pyrazine-2,3-dicarboxyl-[(D-Ser-OH)/(L-Ser-OH)] (18 mg, 0.05 mmol) was then activated in DMF with PyBOP (78 mg, 0.15 mmol), HOBt (20 mg, 0.15 mmol) and NMM (25 μL, 0.225 mmol) and the mixture added to the deprotected resin. This was allowed to react overnight with agitation of the reaction mixture by a stream of nitrogen. The resin was then washed successively with DMF, $CH_2Cl_2$ and $Et_2O$ before drying in vacuo. It was then treated for 1 h with $CF_3COOH$ containing 5% $H_2O$. Resin residue was filtered off, the filtrate was evaporated and the crude peptide product was precipitated by the addition of $Et_2O$. The dried peptide material was redissolved in $H_2O$ and was fractionated by semi-preparative RP-HPLC using a $C_{18}$ column and shallow gradient elution with MeCN gradients in 0.1% aq $CF_3COOH$. Appropriate fractions were collected, pooled, concentrated and re-chromatographed to homogeneity. The analytically correct product showed analytical RP-HPLC: $t_R$=11.34 min (Vydac 218TP54, 1 mL/min, 0 to 20% MeCN in 0.1% aq $CF_3COOH$ over 20 min, λ=215 nm);

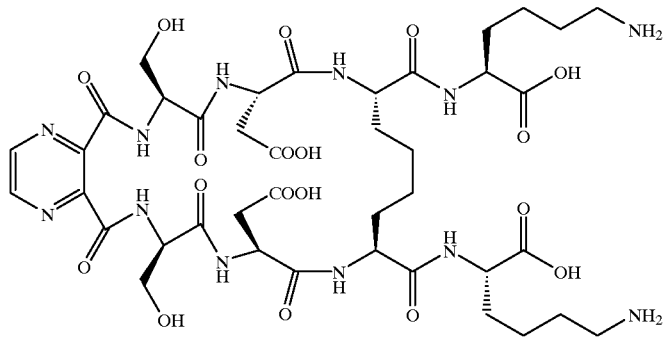

co-chromatography of a sample of Pyrazine-2,3-dicarboxyl-(L-Ser)$_2$-(Asp)$_2$-Dasa-(Lys-OH)$_2$ which was synthesised in a similar fashion showed $t_R$=11.67 min for the di-L-Ser isomer. FAB-MS: [M+H]$^+$=997, $C_{40}H_{60}N_{12}O_{18}$=996.98.

EXAMPLE 11

N,N'-bis-[(tris-(hydroxymethyl)methyl]-pyrazine-2,3-dicarboxamide

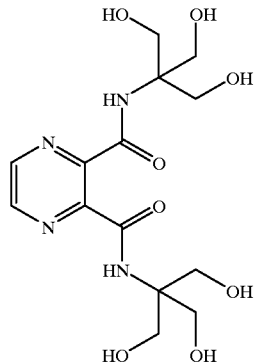

Methyl pyrazine-2,3-dicarboxylate (2 g, 10.2 mmol) was dissolved in EtOH (5 mL). Tris(hydroxymethyl)-aminomethane (2.47 g, 20.4 mmol) was added and the mixture was heated under reflux for 8 h. After cooling, the crystalline title compound (2.54 g, 66.8%) was obtained after filtration, washing with EtOH and drying.

$^1$H-NMR (DMSO): δ=8.78 (s, 2H), 8.00 (s, 2H), 4.61 (t, J=5.8 Hz, 6H), 3.71 (d, J=5.8 Hz, 12H). $^{13}$C-NMR (DMSO): δ=164.68, 145.80, 144.69, 62.70, 60.09. MS: [M+H]$^+$=375.5, $C_{14}H_{22}N_4O_8$=374.36.

EXAMPLE 12

N,N,N',N',-tetrakis(2-hydroxyethyl)pyrazine-2,3-dicarboxamide

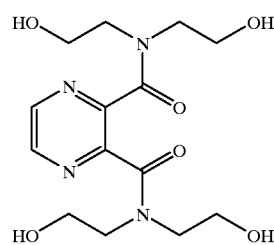

Methyl pyrazine-2,3-dicarboxylate (2 g, 10.2 mmol) was dissolved in EtOH (5 mL). Diethanolamine (2.14 g, 20.4 mmol) was added and the mixture was heated under reflux for 5 h. After cooling the solvent was evaporated and the residue was purified by silica gel chromatography (CHCl$_3$/MeOH, 8:2) to afford the title compound (2.5 g, 71.4%).

$^1$H-NMR (DMSO): δ=8.70 (s, 2H), 4.70 (t, J=5.2 Hz, 2H), 4.67 (t, J=5.6 Hz, 2H), 3.54 (m, 12H), 3.32 (m, 4H). $^{13}$C-NMR (DMSO): δ=166.65, 148.90, 143.27, 59.59, 58.33, 51.57, 48.76. MS: [M+H]$^+$=343.4, $C_{14}H_{22}N_4O_6$=342.36.

EXAMPLE 13

N,N'-bis(1,3-dihydroxyprop-2-yl)pyrazine-2,3-dicarboxamide

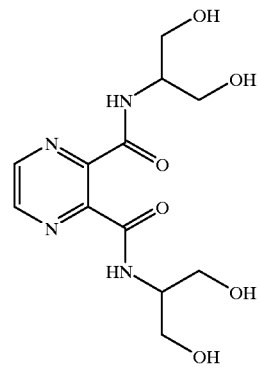

Methyl pyrazine-2,3-dicarboxylate (2 g, 10.2 mmol) was dissolved in EtOH (5 mL). 2-Amino-1,3-propanediol (1.86 g, 20.4 mmol) was added and the mixture was heated under reflux for 4 h. After cooling the solvent was evaporated and the residue was purified by silica gel chromatography (CHCl$_3$/MeOH, 8:2) to afford the title compound (2 g, 62.5%).

$^1$H-NMR (DMSO): δ=8.77 (s, 2H), 8.21 (d,J=8.40 Hz, 2H), 4.61 (t, J=5.80 Hz, 4H) 3.91 (m, 2H) 3.55 (m, 8H). $^{13}$C-NMR (DMSO): δ=164.35, 146.28, 144.58, 59.99, 53.31. MS: [M+H]$^+$=315.4, $C_{12}H_{18}N_4O_6$=314.30.

EXAMPLE 14

N,N'-bis(2-hydroxyethyl)pyrazine-2,3-dicarboxamide

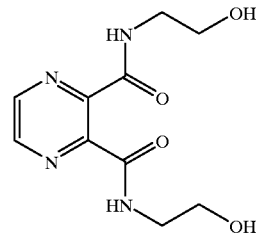

Methyl pyrazine-2,3-dicarboxylate (2 g, 10.2 mmol) was dissolved in EtOH (3 mL). Ethanolamine (1.25 g, 20.4 mmol) was added and the mixture was heated under reflux for 6 h. After cooling the solvent was evaporated and the residue was purified by silica gel chromatography (EtOAc/MeOH, 3:1) to afford the title compound (1.7 g, 65.4%).

$^1$H-NMR (DMSO): δ=8.76 (S, 2H), 8.49 (t,J=6.0 Hz, 2H), 4.70 (br. s, 2H), 3.53 (t, J=6.3 Hz, 4H), 3.33 (m, 4H). $^{13}$C-NMR (DMSO): δ=164.66, 146.60, 144.56, 59.72, 41.83.

EXAMPLE 15

Pyrazine-2,3-dicarboxyl morpholine diamide

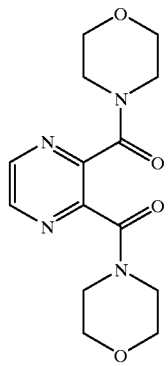

Pyrazine-2,3-dicarboxylic acid (1 g, 5.95 mmol) was suspended in $CH_2Cl_2$ (50 mL). Morpholine (1.04 g, 11.9 mmol) and HOBt (2.37 g, 15 mmol) were added and the mixture was cooled to 0° C. DCC (2.46 g, 11.9 mmol) was then added and the reaction mixture was allowed to reach ambient temperature overnight. The formed dicyclohexylurea was filtered off and the filtrate was evaporated. The residue was purified by silica gel chromatography ($CHCl_3$/MeOH, 19:1) to afford the title compound (1.43 g, 78.6%).

$^1$H-NMR ($CDCl_3$): δ=8.54 (s, 2H), 3.78 (s, 8H), 3.74 (t, J=5.0 Hz, 4H), 3.45 (t, J=5.0 Hz, 4H). $^{13}$C-NMR ($CDCl_3$): δ=165.28, 149.97, 142.73, 47.60, 42.51.

EXAMPLE 16

Pyrazine-2,3-dicarboxyl benzyliminodiacetate diamide

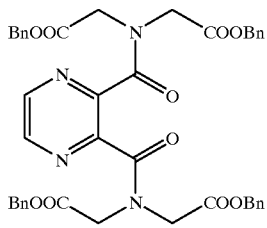

(a) Boc-Iminodiacetic acid

Iminodiacetic acid (3 g, 22.5 mmol) was dissolved in a mixture of 2 M NaOH (25 muL), $H_2O$ (25 mL) and dioxane (25 mL). The solution was cooled to 0° C. and a solution of $Boc_2O$ (5.46 g, 25 mmol) in dioxane (25 mL) was added all at once. The reaction was allowed to proceed at ambient temperature overnight. The solution was then concentrated to 50 mL and its pH adjusted to 2 with 5% aq $KHSO_4$. It was extracted with EtOAc, dried over $MgSO^4$ and evaporated to afford the title compound (5.07 g, 96.6 g).

$^1$H-NMR (DMSO): δ=3.91 (s, 2H), 3.88 (s, 2H), 1.36 (s, 9H). $^{13}$C-NMR (DMSO): δ=171.21, 154.87, 79.68, 49.76, 49.23, 27.93

(b) Boc-Iminodiacetic acid dibenzyl ester

Boc-Iminodiacetic acid (5 g, 21.44 mmol), 4-dimethylaminopyridine (5.24 g, 42.87 mol), benzyl alcohol (4.64 g, 42.9 mmol) and HOBt (6.8 g, 43 mmol) were dissolved in $CH_2Cl_2$ (200 mL) and the solution was cooled to 0° C. DCC (8.84 g, 42.9 mmol) was added and the reaction was allowed to proceed at ambient temperature overnight. Precipitated dicyclohexylurea was filtered off and the filtrated was extracted with 4% aq $NaHCO_3$.

The organic phase was dried over $MgSO_4$ and evaporated. The residue was purified by silica gel chromatography (petroleum ether/EtOAc, 3:1) to afford the title compound (4.6 g, 52.3%).

$^1$H-NMR ($CDCl_3$): δ=7.34 (m, 10H), 5.17 (s, 2H), 5.16 (s, 2H), 4.17 (s 2H), 4.05 (s, 2H), 1.39 (s, 9H). $^{13}$C-NMR ($CDCl_3$): δ=169.67, 169.54, 155.04, 135.46, 128.61, 128.58, 128.46, 128.36, 128.24, 81.19, 66.86, 66.81, 49.81, 49.23, 28.10.

(c) Imino diacetic acid debenzyl ester hydrochloride

Boc-Iminodiacetic acid dibenzyl ester (4.5 g, 10.88 mmol) was dissolved in dioxane (15 mL), then 4.6 M HCl in dioxane (20 mL) was added. The mixture was stirred for 90 min at room temperature and $Et_2O$ (200 mL) was added. The crystalline product was filtered off, washed twice with $Et_2O$ and dried in vacuo to afford the title compound (3.58 g, 94.2%).

$^1$H-NMR (DMSO): δ=10.0 (br. s, 2H), 7.4 (m, 10H), 5.25 (s, 4H), 4.07 (s, 4H). $^{13}$C-NMR (DMSO): δ=166.55, 135.23, 128.60, 128.51, 128.34, 67.10, 46.73.

(d) Pyrazine-2,3-dicarboxyl benzyliminodiacetate diamide

Pyrazine-2,3-dicarboxylic acid (0.72 g, 4.29 mmol), iminodiacetic acid dibenzyl ester hydrochloride (3 g, 8.58 mmol), $Pr^i_2NEt$ (1.11 g, 8.6 mmol) and HOBt (237 g, 15 mol) were dissolved in $CH_2Cl_2$ (70 mL) and the solution was cooled to 0° C. Then DCC (1.77 9, 8.6 mmol) was added and the reaction was allowed to proceed overnight at room temperature. The precipitated dicyclohexylurea was then filtered off and the filtrate was extracted with 4% aq $NaHCO_3$. The organic phase was dried over $MgSO_4$ and evaporated. The residue was purified by silica gel chromatography (petroleum ether/EtOAc, 1:1) to afford the title compound (2.13 g 67%).

$^1$H-NMR ($CDCl_3$): δ=8.19 (s, 2H), 7.33 (m, 20H), 5.17 (s, 4H), 5.16 (s, 4H), 4.48 (s, 4H), 4.25 (s, 4H). $^{13}$C-NMR ($CDCl_3$): δ=168.53, 168.19, 166.40, 149.04, 142.78, 135.47, 135.38, 128.60, 128.58, 128.54, 128.46, 128.37, 128.30, 66.97, 51.24, 48.27.

EXAMPLE 17

N,N'-bis(Diethylmalonyl)pyrazine-2,3-dicarboxamide

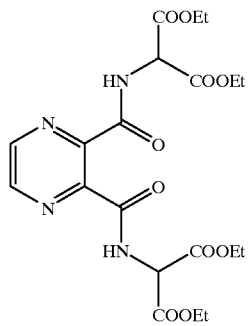

Pyrazine-2,3-dicarboxylic acid (3.97 g, 23.5 mmol) was suspended in $CH_2Cl_2$ (300 mL). Diethylmalonate hydrochloride (10 g, 47.25 mmol), HOBt (7.9 g, 50 mmol and $Pr^i_2NEt$ (6.2 g, 48 mmol) were added and the solution was cooled to 0° C. 1-ethyl-3-(3'-dimethylaminopropyl) carbodiimide (9.2 g, 48 mmol) was then added and the reaction was allowed to proceed overnight at room temperature. The mixture was extracted with 4% aq $NaHCO_3$ and the organic phase was dried over $MgSO_4$ and evaporated. The residue was purified by silica gel chromatography (petroleum ether/EtOAc, 1:1) to afford the title compound (7.58 g, 60%).

$^1$H-NMR ($CDCl_3$): $\delta$=8.71 (s, 2H), 7.93 (d, J=7.6 Hz, 2 H), 5.39 (d, J=7.5 Hz, 2H), 4.29 (m, 8H), 1.31 (t, J=7.2 Hz, 12H). $^{13}$C-NMR ($CDCl_3$): $\delta$=165.84, 163.44, 145.77, 144.63, 62.71, 56.60, 13.96.

EXAMPLE 18

N,N,N',N'-tetrakis(2-hydroxyethyyl)pyridine-2,3-dicarboxamide

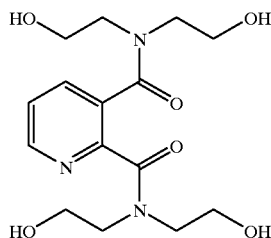

Pyridine-2,3-dicarboxylic acid dimethyl ester (2 g, 10.25 mmol) was dissolved in EtOH (5 mL). Diethanolamine (2.16 g, 20.5 mmol) was added and the mixture was heated under reflux for 6 h. After cooling the solvent was evaporated and the residue was purified by silica gel chromatography ($CHCl_3$ MeOH, 8:2) to afford the title compound (1.99 g, 57%)

$^1$H-NMR (DMSO): $\delta$=8.57 (m, 1H), 7.91 (m, 1H), 7.49 (m, 1H), 4.70 (m, 4H), 3.57 (m, 4H), 3.51 (m, 8H), 3.31 (t, J=6.3 Hz, 2H), 3.23 (t, J=5.8 Hz, 2H). $^{13}$C-NMR (DMSO): $\delta$=168.52, 168.02, 152.15, 148.31, 135.44, 131.69, 123.62, 59.50, 58.59, 58.42, 58,17, 51.90, 51.55, 48.63, 47.61.

EXAMPLE 19

N,N'-bis(1,3 dihydroxyprop-2-yl)pyridine-2,3-dicarboxamide

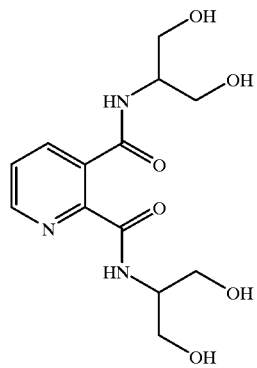

Pyridine-2,3-dicarboxylic acid dimethyl ester (2 g, 10.25 mmol) was dissolved in EtOH (5 mL). 2-Amino-1,3-propanediol (1.87 g, 20.5 mmol) was added and the mixture was heated under reflux for 6 h. After cooling the solvent was evaporated and the residue was purified by silica gel chromatography ($CHCl_3$/MeOH, 7:4) to afford the title compound (4 g, 75%).

$^1$H-NMR (DMSO): $\delta$=8.64 (m, 1H), 8.33 (d, J=8.6 Hz, 1H), 7.91 (d, J=8.4 Hz, 1H), 7.85 (m, 1H), 7.61 (m, 1H), 4.75 (t, J=5.4 Hz, 2H), 4.45 (t, J=5.9 Hz 2H), 3.889 (m, 2H), 3.50 (m, 8H). $^{13}$C-NMR (DMSO): $\delta$=167.64, 163.88, 148.44, 146.96, 137.14, 133.85, 125.88, 60.47, 59.83, 53.89, 52.90.

EXAMPLE 20

Pyrazine-2,3-dimethyl-di-[D-Ser-OH]

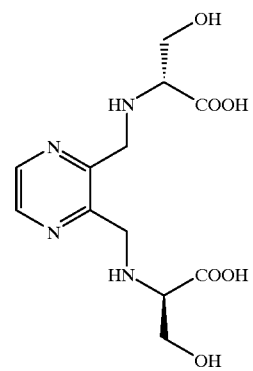

2,3-Bis(chloromethyl)pyrazine was prepared from 2,3-dimethylpyrazine by free radical chlorination (see G. R. Newkome et al., Synthesis, 1984, 676–679) and was purified by silica gel chromatography ($CH_2Cl_2$/EtOAc, 10:1). H-D-Ser(Bu$^t$)-OBu$^t$ (0.58 g, 2.26 mmol) and NMM (0.35 mL, 3.4 mmol) were dissolved in $CH_2Cl_2$ (5 mL). To the stirring solution 2,3-bis(chloromethyl)pyrazine (0.1 g, 0.57 mmol) in $CH_2Cl_2$(1 mL) was added and the entire mixture was left stirring at ambient temperature for 2 days. The mixture was then diluted with $CH_2Cl_2$ to 30 mL and extracted successively with 5% aq $NaHCO_3$ (3×10 mL) and $H_2O$ (1×10 mL). The organic fraction was then evaporated and redissolved in CF₃COOH (15 mL). After stirring for 0.5 hours, the reaction mixture was evaporated and the residue was dissolved in H₂O. This solution was extracted several times with Et₂O. The aqueous portion was fractionated directly on a RP-HPLC column (Vydac 201HS1022) by application of a solvent gradient of 0 to 5% MeCN in 0.1% aq CF₃COOH at 10 mL/min over 30 minutes. Fractions containing the desired product were pooled. Further fractions containing incompletely deprotected (t-butyl groups still present by NMR) product were also pooled, lyophilised and further treated with CF₃COOH for 1.5 hours. After work-up as above, both portions of product were combined and purified to homogeneity by RP-HPLC (column as above) using isocratic elution at 5 mL/min with 0.1 aq CF₃COH. Appropriate fractions were pooled and lyophilised to afford pure title compound (7 mg). Analytical RP-HPLC: $t_R$=3.0 min (Vydac 201HS54, 4.6×250 mm, 1 mL/min, 0 to 20% MeCN in 0.1% aq CF₃COOH over 20 min, $\lambda$=215 nm).

FAB-MS: $[M+H]^+$=315.3. $C_{12}H_{18}O_6N_4$=314.30¹-NMR (DMSO): $\delta$=3.86 (m, Ser C$^\beta$$\underline{H}_2$, 4H), 3.95 (m, Ser C$^\alpha$$\underline{H}$, 2H), 4.4 (s, Ar-C$\underline{H}_2$, 4H), 8.65 (s, Ar—H, 2H).

EXAMPLE 21

Pyrazine-2,3-dicarboxyl-di-([D-Ser]-benzyl ester)

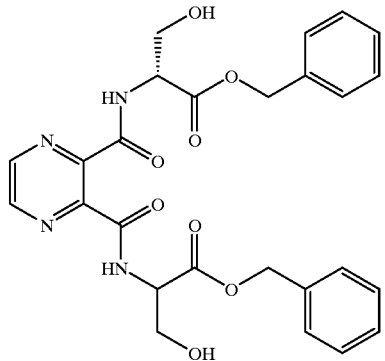

D-Serine benzyl ester hydrochloride (0.93 g, 4 mmol) was dissolved in DMF (20 mL) and NMM (0.4 mL, 4 mmol) was added. The mixture was added to a prepared solution of pyrazine-2,3-dicarboxylic acid (0.17 g, 1 mmol), O-(7-azabenzotriazol-1-yl)-1,1,3,3-tetramethyluronium hexafluorophosphate (0.76 g, 2 mmol) and NMM (0.4 mL, 4 mmol) in DMF (10 mL). The resulting solution was stirred during 2.5 hours. DMF was then removed in vacuo and the residue was partitioned between CH₂Cl₂ and 5% aq NaHCO₃. The organic phase was further extracted with 5% aq NaHCO₃, 5% aq citric acid and H₂O before being dried over Na₂SO₄, filtered and evaporated. The residue was crystallised from hexane/Pr$^i$OH (1:1), filtered, washed with Et₂O and dried. The resulting material was redissolved in MeCN/H₂O (3:1) and the solution was lyophilised to afford the pure title compound.

MALDI-TOF MS: $[M+H]^+$=523.3; $C_{26}H_{26}O_8N_4$=522.51; ¹H-NMR (DMSO): $\delta$=3.72–3.88 (dm, Ser C$^\beta$$\underline{H}_2$, 4H), 4.62 (m, Ser C$^\alpha$$\underline{H}$, 2H), 5.16 (s, Ar—C$\underline{H}_2$, 4H), 7.29–7.40 (m, Ar—H benzyl, 10H), 8.81 (s, Ar—H pyrazine, 2H).

EXAMPLE 22

Pyrazine-2-[N-bis-(2-hydroxyethyl)-carboxamide]-3-[N-(2-methyl-1,3-pronanediol-2-yl]-carboxamide

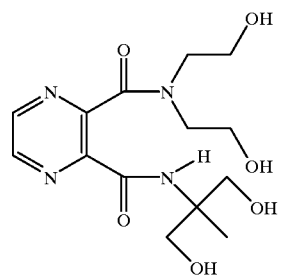

(a) Pyrazine-2,3-dicarboxylic acid dimethylester

A solution of pyrazine-2,3-dicarboxylic acid (50 g, 297.50 mmol) in 300 mL methanol and 15 mL concentrated sulfuric acid was refluxed for 24 hours. The solution was concentrated to remove MeOH, the residue redissolved in 450 mL ethylacetate and the solution extracted with 450 mL saturated NaHCO₃. The organic phase was then successively extracted with 450 mL H₂O, dried over anhydrous Na₂SO₄, filtered and evaporated to dryness. Pyrazine-2,3-dicarboxylic acid dimethylester was isolated as an orange oil (46.9 g, 80%).

¹³C-NMR (CDCl₃) $\delta$ 164.32, 145.20, 144.41, 52.90.
(b) Pyrazine-2-[N-bis-(2-hydroxyethyl)-carboxamide]-3-[N-(2-methyl-1,3-propanediol-2-yl]-carboxamide A solution of pyrazine-2,3-dicarboxylic acid dimethylester (0.25 g, 1.27 mmol), 2-amino-2-methylpropane-1,3-diol (0.132 g, 1.26 mmol) and diethanolamine (0.134 g, 1.27 mmol) in 15 mL ethanol was refluxed for 24 hours and the solvent removed in vacuo. The residue (0.26 g) was prepurified using 90 g silica gel 60 (35–70 mesh) and CH₂Cl₂/MeOH (5:1). The remaining 120 mg were purified using silica gel 60 (20–45 mesh) and methylethylketone/methanol (40:5). Yield: 38 mg of pure compound.

¹³C-NMR (DMSO-d₆): $\delta$ 167.21, 162.15, 149.87, 146.36, 143.13, 142.33, 63.43, 59.15, 58.32, 58.28, 51.15, 48.03, 18.07.

EXAMPLE 23

Pyrazine-2-[N-bis-(2-hydroxyethyl)-carboxamide]-3-[N-tris-(hydroxymethyl)-methyl]-carboxamide

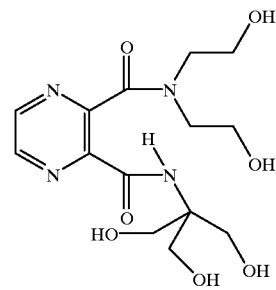

A solution of pyrazine-2,3-dicarboxylic acid dimethylester (5.5 g, 28.04 mmol), tris-(hydroxymethyl)- aminomethane (3.4 g, 28.07 mmol) and diethanolamine (2.85 g, 27.11 mmol) in 60 mL ethanol was refluxed for 24 hours and the solvent removed in vacuo. The crude product (11.72 g) was purified using 90 g of silica gel 60 (35–70 mesh) with $CH_2Cl_2$/MeOH (5:1). After evaporation the residue was redissolved in 5 mL $H_2O$ and the solution lyophilised to yield 200 mg of the title compound as yellowish powder.

$^{13}$C-NMR (DMSO-$d_6$): δ 170.72, 164.80, 151.02, 147.93, 145.03, 143.79, 63.78, 62.45, 61.05, 60.45, 53.40, 50.29.

EXAMPLE 24

Pyrazine-2-[N-(2-methyl-1,3-propanediol-2-yl)]-3-{N-[tris-(hydroxymethyl)]-methyl}-carboxamide

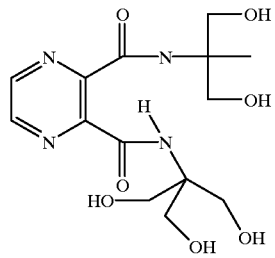

A solution of pyrazine-2,3-dicarboxylic acid dimethylester (5.5 g, 28.04 mmol), tris-(hydroxymethyl)-aminomethane (3.4 g, 28.07 mmol) and 2-amino-2-methylpropane-1,3-diol (2.85 g, 27.11 mmol) in 60 mL ethanol was refluxed for 24 hours and the solvent removed in vacuo. The crude product (11.24 g) was purified over 90 g silica gel 60 (35–70 mesh) and $CH_2Cl_2$/MeOH (5:1). After evaporation the residue was redissolved in 5 ml $H_2O$ and the solution lyophilised to yield 260 mg of the title compound as yellowish powder.

$^{13}$C-NMR (DMSO-$d_6$): δ 164.71, 164.40, 145.99, 145.92, 144.69, 63.52, 62.72, 60.07, 58.94, 18.36.

What is claimed is:

1. Compounds of formula I:

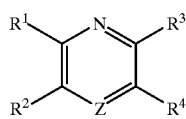

(I)

(wherein
R$^1$ represents a group

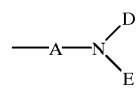

or —G—D;
one of R$^2$, R$^3$ and R$^4$ represents a group as defined above for R$^1$ which may be the same as or different from R$^1$ and the remaining two of R$^2$, R$^3$ and R$^4$ independently represent a hydrogen atom or a $C_{1-6}$ alkyl group;

Z represents —N— or —CH—;
A represents —CO— or —$CH_2$—;
G represents cis or trans —CH=CH— or a group of the formula

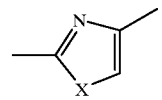

in which X represents —O—, —S—, —NH— or —$CH_2$—;
D represents a group —$CR^5R^6R^7$ or —$CR^8[(CH_2)_l$—X']$_2$ in which
R$^5$ represents —H or a $C_{1-4}$ alkyl group optionally substituted by a hydroxy, $C_{1-4}$ alkoxy, carboxy, phenyl or hydroxyphenyl group, such as —$CH_3$, —$CH_2OH$, —$CH_2OCH_3$, —$CH(CH_3)OH$, —$(CH_2)_2$OH, —$CH_2(C_6H_4)OH$, —$CH_2CO_2H$ or —$(CH_2)_2CO_2H$;
R$^6$ represents —H or —$CH_3$;
R$^7$ represents —$CO_2R^9$ or —$CONR^9R^9$;
R$^8$ represents —H or a $C_{1-6}$ alkyl group optionally substituted by a hydroxyl group;
X' represents —OH, —$NH_2$, —$CO_2R^9$ or —$CONR^9R^9$;
each R$^9$ independently represents —H or a $C_{1-6}$ alkyl group;
l is 0 or an integer from 1 to 5;
E represents —H, —OH or $C_{1-6}$ alkyl;
or D and E each represents a group —$(CH_2)_k$—X' or —$(CH_2)_k$—$CO_2R^{10}$ in which k is an integer from 1 to 5, X' has the above meaning and R$^{10}$ represents a $C_{7-10}$ aralkyl group;
or D and E together with the intervening nitrogen atom form a heterocyclic group of formula

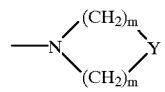

in which each m independently represents an integer from 1 to 3;
Y represents —O—, —NH—, —S—, —SO— or —$SO_2$—)
and physiologically acceptable salts thereof.

2. Compounds as claimed in claim 1 wherein R$^1$ and R$^2$ are both

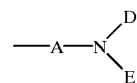

or —G—D.

3. Compounds as claimed in claim 1 wherein Z is —N—; R$^1$ and R$^2$ are

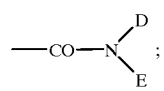

and R$^3$ and R$^4$ are —H.

4. Compounds as claimed in claim 1 of formula (1), (2) or (3):

(1)
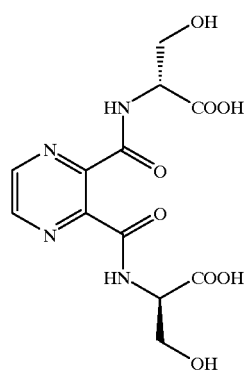

Pyrazine-2,3-dicarboxyl-di[D-Ser-OH]:

(2)
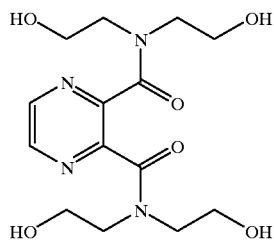

N,N,N',N'-tetrakis(2-hydroxyethyl)pyrazine-2,3-dicarboxamide:

(3)
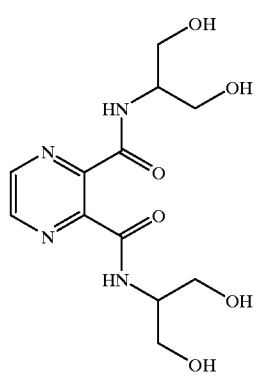

N,N'-bis(1,3-dihydroxyprop-2-yl)pyrazine-2,3-dicarboxamide.

5. A pharmaceutical composition comprising a compound as claimed in claim 1 together with a pharmaceutical carrier or excipient.

6. Compounds as claimed in claim 1 for use in regulating haematopoiesis.

7. A method of regulation of haematopoiesis in a human or non-human animal body, said method comprising administering to said body an effective amount of a composition as claimed in claim 5.

8. A process for preparing a compound as claimed in claim 1, said process comprising any one of the following steps:

(a) (in order to prepare compounds of formula I in which $R^1$ and one of $R^2$, $R^3$ and $R^4$ represents

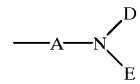

in which A is —CO—) reacting the corresponding pyridine or pyrazine 2,3-, 2,5- or 2,6-dicarboxylic acids, esters or an activated derivative thereof with a group of formula II (II)
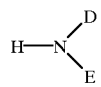

(wherein D and E are as defined in claim 1);

(b) (in order to prepare compounds of formula I in which $R^1$ and one of $R^2$, $R^3$ and $R^4$ represents

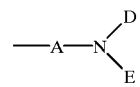

in which A is —CH$_2$—) reacting the corresponding pyridine or pyrazine 2,3-, 2,5- or 2,6-bis(chloromethyl) derivative with a group of formula II as hereinbefore defined;

(c) (in order to prepare compounds of formula I in which $R^1$ and one of $R^2$, $R^3$ and $R^4$ represents —G—D in which G is cis or trans —CH=CH—) reacting the corresponding pyridine or pyrazine 2,3-, 2,5- or 2,6-dialdehyde with a phosphorus ylid of formula III (III)
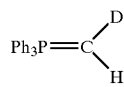

such a pyridine or pyrazine dialdehyde may conveniently be obtained from the corresponding dicarboxylic acids, diacid derivatives, dialcohols, diacetals etc., (d) (in order to prepare compounds of formula I in which $R^1$ and one of $R^2$, $R^3$ and $R^4$ represents —G—D in which G is a group of formula

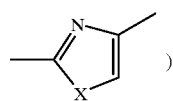

reacting the corresponding pyridine or pyrazine 2,3-, 2,5- or 2,6-dicarboxylic acids or an activated derivative thereof such as imino esters, nitriles etc. with a group of formula IV

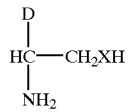

(IV)

(wherein X and D are as defined in claim 1) followed where necessary by oxidation;

(e) converting a compound of formula I as prepared in any one of steps (a) to (d) into a salt thereof; and (f) resolving a chiral compound of formula I into its isomers.

9. A process for preparing a compound as claimed in claim 1, said process comprising deprotecting a partially or fully protected derivative of a compound of formula I.

* * * * *